United States Patent [19]
Walch et al.

[11] Patent Number: 5,702,447
[45] Date of Patent: Dec. 30, 1997

[54] DEVICE FOR THE ATTACHMENT OF A GLENOID PROSTHESIS OF THE SHOULDER BLADE

[75] Inventors: Gilles Walch, Lyons; Pascal Boileau, Nice, both of France

[73] Assignee: Tornier S.A., Saint-Ismier, France

[21] Appl. No.: 758,030

[22] Filed: Nov. 27, 1996

[30] Foreign Application Priority Data

Nov. 30, 1995 [FR] France ................... 95 14454

[51] Int. Cl.[6] ............................................. A61F 2/28
[52] U.S. Cl. ........................... 623/16; 623/18; 623/19; 606/72; 606/73
[58] Field of Search ................... 623/16, 17, 18, 623/19, 20; 606/60, 61, 72, 73

[56] References Cited

U.S. PATENT DOCUMENTS

| | | | |
|---|---|---|---|
| 3,805,775 | 4/1974 | Fisher et al. | 606/68 |
| 4,091,806 | 5/1978 | Aginsky | 606/63 |
| 4,167,047 | 9/1979 | Grundei et al. | 623/20 |
| 4,479,271 | 10/1984 | Bolesky et al. | 623/18 X |
| 5,032,132 | 7/1991 | Matsen, III et al. | 623/19 |
| 5,080,673 | 1/1992 | Burkhead et al. | 623/19 |
| 5,152,797 | 10/1992 | Luckman et al. | 623/20 |
| 5,360,450 | 11/1994 | Giannini | 623/16 X |
| 5,593,448 | 1/1997 | Dong | 623/19 |

FOREIGN PATENT DOCUMENTS

| | | |
|---|---|---|
| 0393543 | 10/1990 | European Pat. Off. . |
| 0495340 | 7/1992 | European Pat. Off. . |
| 2615726 | 12/1988 | France . |

Primary Examiner—Mary Beth Jones
Attorney, Agent, or Firm—Dowell & Dowell

[57] ABSTRACT

A device for attaching a prosthesis including a metal foundation provided with a plate integrally formed with at least one anchoring pin consisting of elastically deformable wings and at least one the screw cooperating with a nut. The screw goes through the pin, to spread the wings into a position away from a longitudinal axis of the pin. The anchoring pin comprises an internal bore having a cylindrical base connecting the pin to the plate, and a circular counter-bore adjacent the bore of greater diameter than the internal bore of the pin, making it possible to spread the wings while maintaining their rigidity over their entire length.

13 Claims, 3 Drawing Sheets

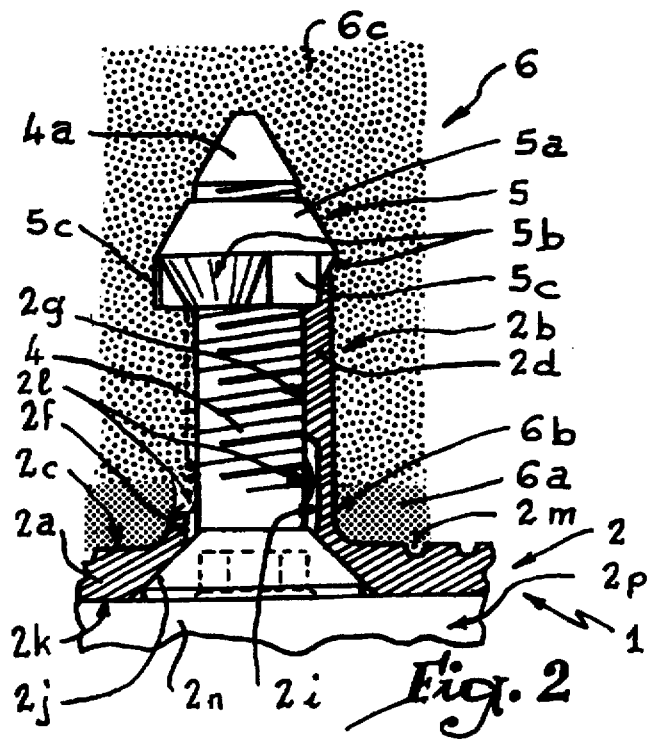
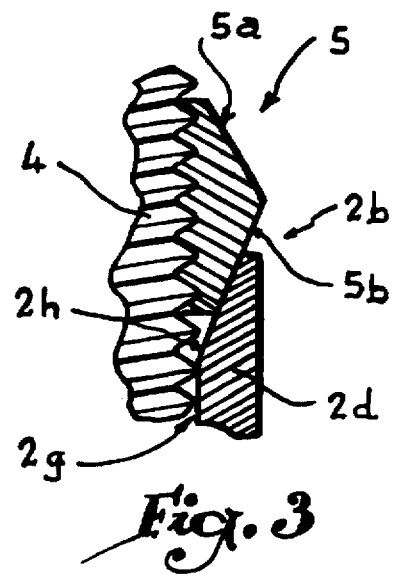
Fig. 2
Fig. 3
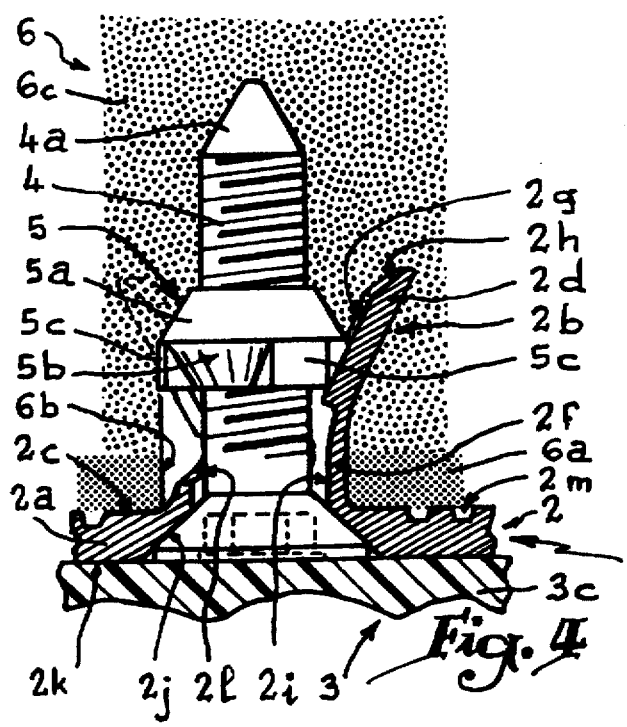
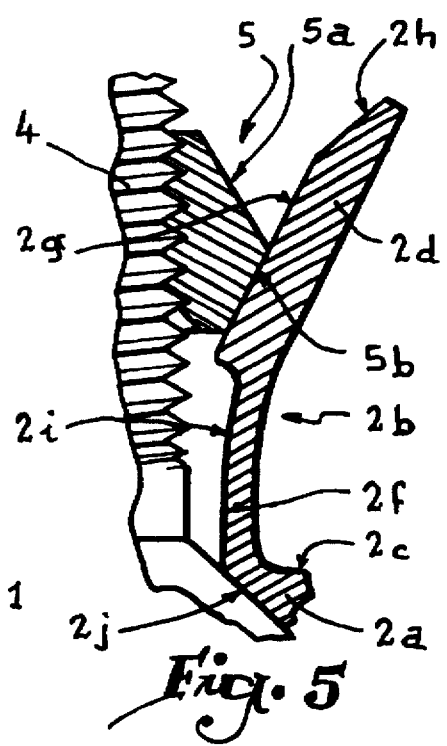
Fig. 4
Fig. 5

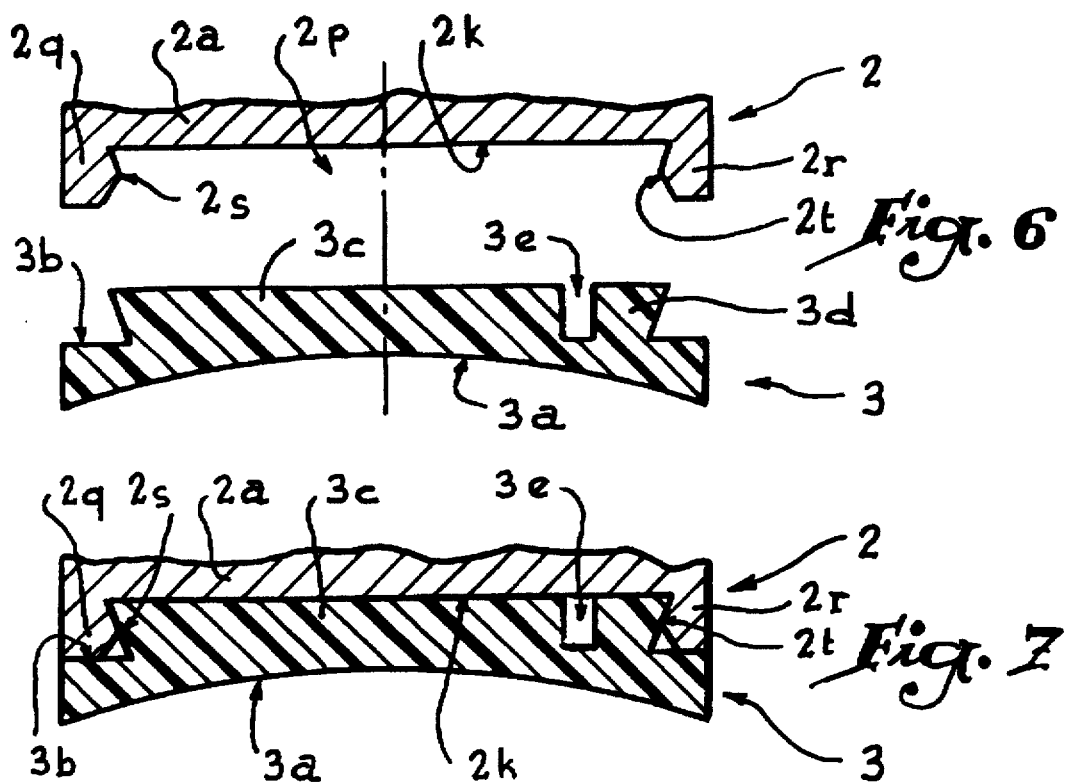
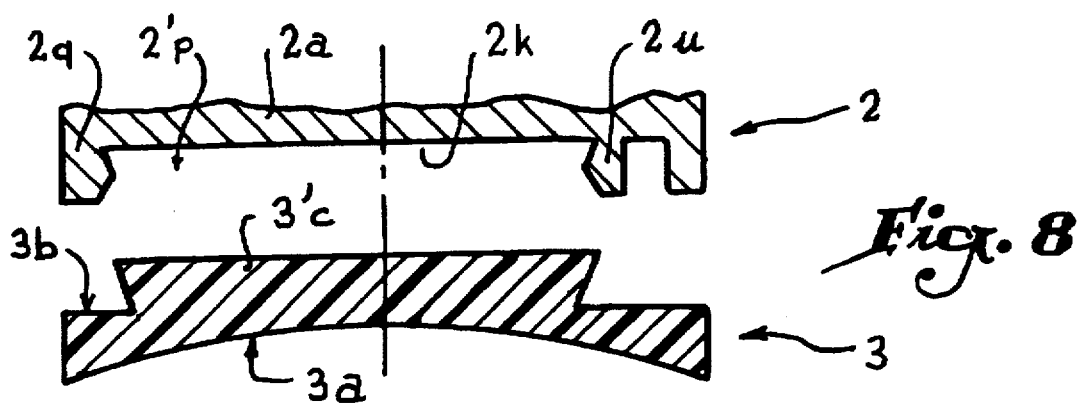
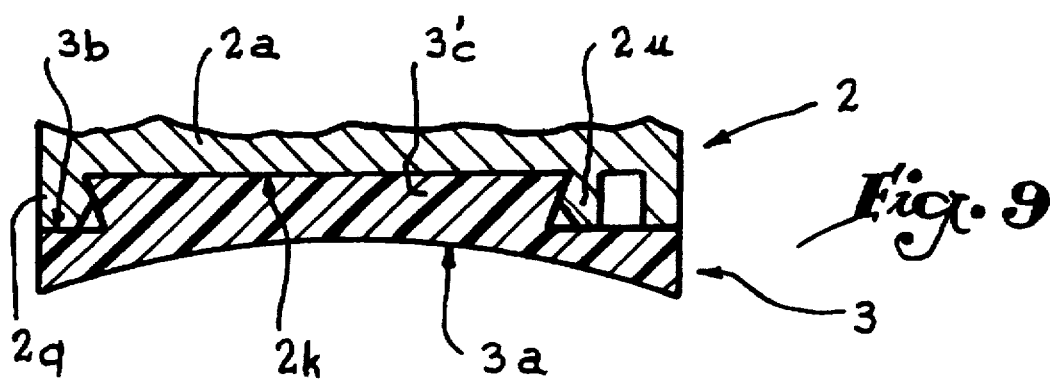

5,702,447

DEVICE FOR THE ATTACHMENT OF A GLENOID PROSTHESIS OF THE SHOULDER BLADE

BACKGROUND OF THE INVENTION

1. Field of the Invention

The present invention relates to a device making it possible to attach a prosthesis in the bone of a patient and, more specifically, to attach a glenoid prosthesis of the shoulder blade.

2. History of the Related Art

Fastening devices are known that comprise either screws or a binder such as cement to maintain a prosthetic element against the bone. In the case of glenoid protheses, devices are known comprising a metal foundation that is fastened on the bone by screws or by fluted anchoring pins. The fastening screws make it possible to put the bone in compression under the metal foundation of the prosthesis. On the other hand, when the metal foundation comprises anchoring pins, these do not allow the bone to be put in compression.

The fluted anchoring pins can be hollow and slit, and after insertion in holes in the bone, they can receive on the inside a female part that slightly increases the diameter of the pins in order to exert a constraint on the bone without deforming it. Thus, the anchoring of the metal foundation of the prosthesis is obtained by enlarging the initial dimensions of the anchoring pins.

When the metal foundation comprises fastening screws, it is noted that putting them in place is not as easy and that there is a risk of migration of the screws by settling of the bones, causing the ejection of a plastic insert constituting an articular surface.

On the other hand, when the metal foundations are formed as one piece with the anchoring pins, it is noted that putting them in place is easier, but the disadvantage with them is that they do not put the bone in compression under the prosthesis, causing a destabilization of the prosthesis with the passing of time.

Known from French Patent Application No. FR-A-2615726 is a prosthetic fastening element with anchoring pin, in which a screw can be inserted into the anchoring pin. The spreading of wings associated with the pin is not effectively controlled because the spreading occurs solely owing to the pin's elasticity. The wings therefore cannot be very rigid. Now then, when a prosthesis must be put in place in a hard bone, such as a shoulder blade, the use of wings that are not very rigid is not suitable.

SUMMARY OF THE INVENTION

The present invention is aimed more specifically at remedying the disadvantages set forth above.

The purpose of the present invention is to design a metal foundation comprising elastically deformable means to compress spongy bone between a cortical part and a metal foundation; these means can be rigid over their entire length.

The fastening device according to the present invention comprises a metal foundation provided with a plate forming one piece with at least one anchoring pin consisting of elastically deformable wings. At least one screw, cooperating with a nut, is provided that goes through the pin to spread the wings into a position away from the longitudinal axis of the pin. The anchoring pin comprises an internal bore having, at a cylindrical base connecting the pin to the plate, a circular housing or counter-bore of greater diameter than the internal bore. The housing makes it possible to spread the wings while maintaining their rigidity over their entire length.

Due to the invention, the spreading of the wings is obtained by the cooperation of the nut and the screw. The wings can be made of a rigid material, because they are deformed only at the circular housing which is of greater diameter, i.e., in a portion where they are less thick.

In addition, the fastening device comprises at least one pin provided with at least three wings delimited by slots that are parallel to the longitudinal axis of the pin.

BRIEF DESCRIPTION OF THE DRAWINGS

The attached drawings, provided as an example, will make it possible to better understand the invention, the characteristics it presents and the advantages it is capable of providing:

FIGS. 2 and 3 are partial views showing the fastening device before the spreading of the wings of the anchoring pin;

FIGS. 4 and 5 are partial views identical to those of FIGS. 2 and 3, but showing the anchoring pin in a spread position;

FIGS. 6 and 7 are cross-sections showing the locking of the plastic insert on the metal foundation of the device according to the present invention;

FIGS. 8 and 9 are cross-sections similar to those of FIG. 6, but showing a variant of fastening of the insert on the metal foundation.

DESCRIPTION OF THE PREFERRED EMBODIMENT

Figure 1:
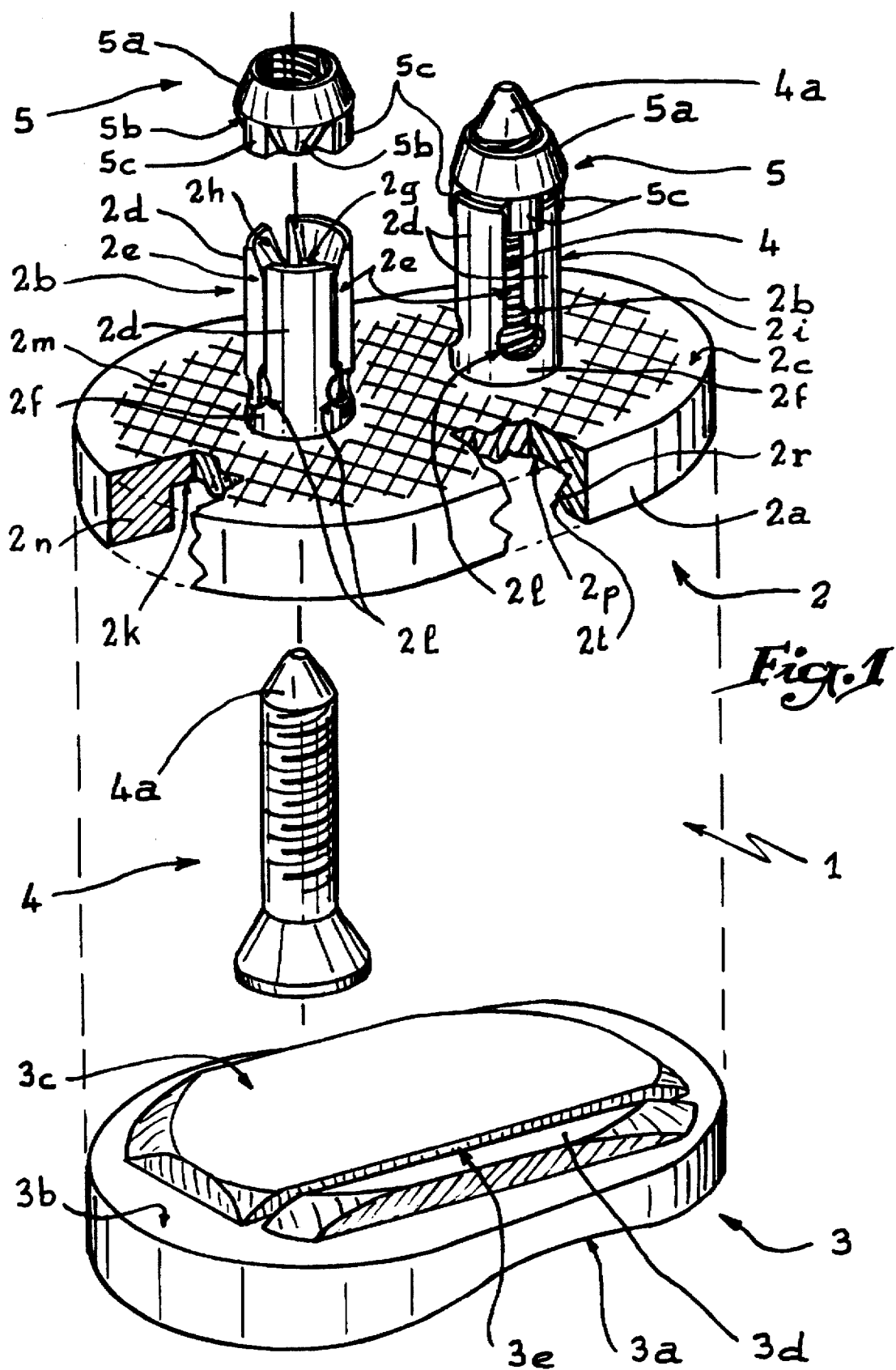
FIG. 1 is an exploded view illustrating the fastening device according to the present invention.

FIG. 1 shows a fastening device 1 comprising a metal foundation 2 intended to receive a polyethylene insert 3 and, in particular, a glenoid prosthetic implant of the shoulder blade. The metal foundation 2 consists of a plate 2a that forms one piece with at least one anchoring pin 2b extending perpendicular to a bearing surface 2c of the plate.

The anchoring pin 2b comprises wings 2d that are delimited by slots 2e extending parallel to the longitudinal axis of the pin. The pin comprises three wings 2d evenly distributed over its periphery. The wings 2d of the pin 2b are connected to the bearing surface 2c of the plate 2 by a non-deformable cylindrical base 2f shared by each wing.

It is noted that each of the slots 2e open into a space of greater diameter or counter-bore 21 situated in the vicinity of the non-deformable cylindrical base 2f. The length of the slots 2e is sufficient to avoid deforming the cylindrical base 2f.

The pin 2b comprises an internal bore 2g that has a conical entrance 2h at the free end of each wing 2d. Opposite the conical entrance 2h and, more specifically, at the cylindrical base 2f, the internal bore 2g comprises a circular housing 2i of greater diameter. The bore 2g of the pin 2b opens into a conical recess 2j on the face 2k opposite that 2b of the plate 2a. The conical recess 2j and the bore 2g are intended to receive a screw 4 that cooperates with a nut 5.

The screw 4 has one free end having a conical profile 4a, improving penetration of the pin 2b into the bone.

The nut 5 comprises two oppositely inclined truncated conical surfaces 5a, 5b hereby referred to as flats. The inclined flat 5b comprises on its edge evenly spaced, raised guides or flanges 5c. The guides 5 are spaced so as to correspond to the slots 2e of the pin 2b during tightening of the screw 4 in the nut 5.

It is noted that the flat 5a is inclined identically to the conical profile 4a of the screw 4 to form, when the metal foundation is put in place against the bone, a continuous, pointed profile improving the penetration of pin 2b. The flat 5b is also inclined similarly to the conical entrance 2h of the pin 2b provided on each wing 2d.

The bearing surface 2c of the plate 2a has a network of recesses or projections 2m obtained by machining or by casting. The recesses or projections 2m are in the form of closed holes having a water-drop profile.

FIG. 2 shows the metal foundation 2 placed against the hard layer 6a of a bone 6. The hard or cortical layer 6a is provided beforehand with at least one hole 6b allowing the passage of the corresponding pin 2b, which is associated with a screw 4 and a nut 5 in order for this assembly to penetrate to the inside of the spongy layer 6c of the bone. It is noted that the pin 2b easily penetrates to the inside of the spongy layer, given that the nut 5 and, more specifically, its inclined flat 5a, is situated in the extension of the conical profile 4a of the screw 4.

It is noted that the nut 5 and, more specifically, its inclined flat 5b, is touching the conical entrance 2h of each wing 2d of the pin 2b (FIG. 3). In this position, it is guaranteed that the guides 5c of the nut 5 are seated within and cooperate with the slots 2e of the pin 2b to prevent the nut from turning freely when the surgeon proceeds to tighten the screw 4.

In FIG. 4, the metal foundation 2 is shown definitively immobilized against the bone 6 of a patient. This definitive immobilization is obtained by tightening the screw 4 in nut 5, enabling the nut, because of its profile, to penetrate between the wings 2d to spread them away from the axis of the pin 2b. It is noted that the inclined flat 5b of the nut 5 bears against the face of the internal bore 2g of each wing 2d after their deformation to prevent any vertical displacement of the screw 4 inside the conical recess 2j, thus preventing the ejection of the plastic insert 3 (FIGS. 4 and 5).

Thus, the screw 4 is immobilized by the nut 5 on one side of the plate 2a and by its head on the other side. This arrangement makes it possible to protect the plastic insert 3 forming the articular surface from any upper migration of the screw 4 which could eject the plastic insert from the metal foundation 2a. In their spread positions, the wings 2d of the pin 2b make it possible to compress the spongy layer 6c of the bone 6 between the wings and the hard or cortical layer 6a, thereby improving the solidity of the fastening of the metal foundation 2.

During the penetration of the nut 5 to the inside of the wings 2d of the pin 2b, it is noted that the cylindrical base 2f undergoes no deformation, to thus avoid breaking the hard or cortical layer 6a during tightening. Indeed, the housing or counter-bore 2i, which is less thick than the wings 2d, enables the wings to be deformed at the connection with the housing while maintaining their rigidity over their entire length.

In the position of FIG. 4, the wings 2d make it possible to urge the face 2b of the plate 2a against the hard layer 6a of the bone 6. Before tightening the screw 4 in the nut 5, the surgeon adds, in the recesses 2m of the face 2b, spongy bone taken from the humerus, previously prepared in this type of operation. The face 2b is coated by the manufacturer with a fine layer of hydroxylapatite promoting new bone growth which solidifies the anchoring in the course of time.

FIGS. 6 and 7 show a first variation of fastening of the insert 3 on the metal foundation 2 of the fastening device 1. The upper face 2k of the plate 2 is provided with a rim 2n that delimits a tray 2p open toward the top. The rim 2n has two parallel sections 2g, 2r each having ribs 2s, 2t directed toward the inside of the tray 2p.

The plastic or ceramic insert 3 comprises an articular surface 3a, while its contour is identical to that of the metal foundation 2. The insert 3 comprises, on its lower face 3b opposite the articular surface 3a, a projecting part 3c with the same contour as the tray 2p and with a height equal to the depth of the tray in order to fit in the tray. A lip 3d is provided parallel to one of the edges of the projection 3c to allow the locking of the insert 3 inside the tray 2p and between the rims 2n. The lip 3d is obtained by a groove 3e arranged in the foundation 3c of the insert 3 thus providing a certain flexibility for the lip.

It is possible to provide for other configurations for the fastening of the insert 3 on the metal foundation 2 of the fastening device 1. FIGS. 8 and 9 show a second variation of attachment of the insert 3 which is symmetrically opposite the one shown in FIGS. 6 and 7. Indeed, the metal foundation 2 comprises on the inside of a tray 2'p a supple lip 2u allowing the locking of the insert, while the insert 3 has a projecting part 3'c with a shape complementary to that of the tray 2'p.

It is noted that the fastening device 1 can comprise a number of pins 2b that varies depending on a particular case. Each pin 2b can have a number of wings that can vary depending on the pin's diameter.

Accordingly, the invention considerably improves the state of the art by providing a fastening device 1 that is easy to use and ensures the cohesion of the different components with the passing of time, with a very solid anchoring, and also ensuring that the bone 6 is put in compression under the plate 2a.

What is claimed is:

1. A device for fastening a prosthesis against the hard layer of a bone, comprising: a metal foundation including a plate and at least one anchoring pin consisting of elastically deformable wings surrounding an internal bore, at least one screw extending through said at least one anchoring pin, a nut adjustable along said at least one screw to spread said wings into a position away from a longitudinal axis of said at least one anchoring pin, said at least one anchoring pin having a cylindrical base connecting said at least one anchoring pin to said plate, said at least one anchoring pin having a circular counter-bore adjacent said base and communicating with said internal bore and being of greater diameter than said internal bore, said counter-bore making it possible to spread said wings as said nut moves relative to said at least one screw while maintaining rigidity of said wings over their length.

2. The device according to claim 1, characterized in that said cylindrical base is non-deformable.

3. The device according to claim 1, characterized in that said at least one anchoring pin comprises at least three wings delimited by slots extending parallel to the longitudinal axis of said at least one anchoring pin, said slots terminating in spaced relationship from said cylindrical base.

4. The device according to claim 1, characterized in that said at least one anchoring pin has a conical entrance spaced from said base arranged at a free end of said wings.

5. The device according to claim 1, characterized in that said nut has two oppositely inclined flats a first of said flats comprises, on a periphery thereof, spaced, raised and outwardly extending guide flanges.

6. The device according to claim 5, characterized in that said guide flanges are arranged so as to cooperatively seat within said slots in said at least one anchoring pin.

7. The device according to claim 5, characterized in that a second of said flats is inclined identically to a conical end profile of said at least one screw.

8. The device according to claim 1, characterized in that said plate comprises a bearing surface consisting of a network of recesses or projections.

9. The device according to claim 1, characterized in that said plate is intended to receive on a face opposite said bearing surface a plastic or ceramic insert comprising an articular surface.

10. The device according to claim 9, characterized in that said insert is locked in a tray.

11. The device according to claim 10, characterized in that said tray is delimited by a rim having two parallel sections that each have ribs directed toward an inside of said tray.

12. The device according to claim 10, characterized in that said insert comprises a projecting part and a supple lip for locking said projecting part inside said tray.

13. The device according to claim 10, characterized in that the insert comprises a projecting part with a shape complementary to a shape of said tray, and said tray having a supple lip for locking said insert.

* * * * *